(12) United States Patent
Waller et al.

(10) Patent No.: US 10,575,839 B2
(45) Date of Patent: Mar. 3, 2020

(54) SOLENOID OCCLUSION DEVICE

(71) Applicant: University of Kansas, Lawrence, KS (US)

(72) Inventors: Stephen Clifford Waller, Overland Park, KS (US); Alyssa Kirk Rollando, Lawrence, KS (US); Richard Kevin Gilroy, Fairway, KS (US); Philip Lee Johnson, Overland Park, KS (US); James Marion Stiles, Prairie Village, KS (US); Sara Ellen Wilson, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 356 days.

(21) Appl. No.: 15/419,296

(22) Filed: Jan. 30, 2017

(65) Prior Publication Data

US 2017/0135683 A1    May 18, 2017

Related U.S. Application Data

(63) Continuation-in-part of application No. PCT/US2015/042601, filed on Jul. 29, 2015.

(60) Provisional application No. 62/030,458, filed on Jul. 29, 2014, provisional application No. 62/402,117, filed on Sep. 30, 2016.

(51) Int. Cl.
*A61B 17/00* (2006.01)

(52) U.S. Cl.
CPC .... *A61B 17/0057* (2013.01); *A61B 17/00491* (2013.01); *A61B 2017/0065* (2013.01); *A61B 2017/00292* (2013.01); *A61B 2017/00544* (2013.01); *A61B 2017/00641* (2013.01); *A61B 2017/00876* (2013.01); *A61B 2017/00951* (2013.01)

(58) Field of Classification Search
CPC .......... A61B 17/0057; A61B 17/00491; A61B 2017/00292; A61B 2017/00641; A61B 2017/0065; A61B 2017/008746; A61B 2017/00951; A61N 2/02; A61M 2037/0007
See application file for complete search history.

(56) References Cited

U.S. PATENT DOCUMENTS

| 3,995,209 | A | 11/1976 | Weston, Sr. |
| 6,283,951 | B1 * | 9/2001 | Flaherty ................. A61B 17/11 604/164.11 |

(Continued)

OTHER PUBLICATIONS

International Search Report and Written Opinion for PCt/US2015/042601, dated Oct. 29, 2015.

*Primary Examiner* — Diane D Yabut
(74) *Attorney, Agent, or Firm* — Ray Quinney & Nebeker P.C.; Paul N. Taylor

(57) ABSTRACT

The present disclosure relates to devices and methods for delivery of a ferrofluid to a targeted treatment site, such as delivery of a ferroadhesive to a pathological fistula to occlude the fistula. A device includes a catheter having a lumen and a distal opening. A hollow solenoid is coupled to a distal section of the catheter, and a hollow core of the solenoid allows passage of a ferrofluid through the catheter and through the hollow core so that it may exit past the distal end of the hollow solenoid. The solenoid may be selectively actuated to maintain or control the position of the delivered ferrofluid.

20 Claims, 8 Drawing Sheets

(56) References Cited

U.S. PATENT DOCUMENTS

| | | | |
|---|---|---|---|
| 6,315,709 B1 | 11/2001 | Garibaldi et al. | |
| 6,364,823 B1 | 4/2002 | Garibaldi | |
| 6,375,606 B1 | 4/2002 | Garibaldi et al. | |
| 6,409,721 B1 | 6/2002 | Wheelock et al. | |
| 6,414,577 B1 | 7/2002 | Hoffman | |
| 6,511,468 B1* | 1/2003 | Cragg | A61B 17/12022 128/898 |
| 6,540,657 B2 | 4/2003 | Cross, III et al. | |
| 7,218,962 B2* | 5/2007 | Freyman | A61M 37/00 600/13 |
| 2002/0087044 A1 | 7/2002 | Cross, III et al. | |
| 2002/0087177 A1* | 7/2002 | Wallace | A61B 17/12022 606/157 |
| 2004/0133189 A1 | 7/2004 | Sakurai | |
| 2008/0029502 A1* | 2/2008 | You | H05B 3/56 219/212 |
| 2008/0105700 A1* | 5/2008 | Voegele | A61B 17/00491 222/1 |
| 2009/0264920 A1* | 10/2009 | Berenstein | A61B 17/0057 606/213 |

\* cited by examiner

SOLENOID OCCLUSION DEVICE

CROSS-REFERENCE TO RELATED APPLICATIONS

This application is a continuation-in-part of PCT Application Serial No. PCT/US2015/042601, filed Jul. 29, 2015, which claims priority to and the benefit of U.S. Provisional Patent Application Ser. No. 62/030,458, filed Jul. 29, 2014. This application also claims priority to and the benefit of U.S. Provisional Patent Application Ser. No. 62/402,117, filed Sep. 30, 2016, the entireties of which are incorporated herein by reference.

BACKGROUND

Fistulas are abnormal tunnels between two tissues within the body. These pathogenic ducts can lead to health problems if left untreated. They commonly occur in the gastrointestinal tract as well as biliary conduits, and can also be seen in the vascular system. If left untreated, fistulas can cause abscesses, infections and other complications. Typically, a fistula that is unable to heal or which develops abscesses, infections, or other complications requires treatment through an invasive surgical procedure. Currently, fistula treatment requires extensive surgery under general anesthesia, followed by several weeks of recuperation. Such procedures are also typically associated with high patient costs. Further, some patients have poor health conditions and are poor candidates for such surgeries in the first place.

Various forms of glues have been explored for use in less invasive tissue closure methods. Cyanoacrylates are the compounds most commonly used for these purposes. These compounds are generally liquid monomers that polymerize into longer polymer chains upon exposure to moisture. There are several varieties designed for medical use in humans. Problems in using these compounds to treat a fistula arise from the difficulty in maintaining precise control of the glue. In some circumstances, the glue can flow away from the targeted treatment site before setting, which risks damaging, obstructing, or occluding non-targeted tissues or anatomical structures. Likewise, the glue delivery device can become entrapped against or within the treatment site if the glue is injected too slowly relative to the polymerization rate of the glue.

BRIEF SUMMARY

Certain embodiments described herein are directed to a delivery device including a catheter having a lumen extending to a distal opening. The device also includes a solenoid coupled to the catheter at a distal section of the catheter. The solenoid has a hollow core such that the catheter can extend into the hollow core or otherwise connect to the hollow core to allow passage of a ferrofluid through the catheter, through the solenoid, and distally past the delivery device to a targeted treatment site. The solenoid also includes an electrically conductive coil disposed around at least a portion of an outer circumferential surface of the core. The solenoid is configured to selectively provide a magnetic field having strength sufficient to hold or otherwise control a bolus of the ferrofluid at a desired treatment site.

In certain embodiments, a delivery device is configured for delivering a ferroadhesive to a targeted pathological fistula in order to occlude the fistula. The delivery device includes a catheter having a lumen extending to a distal opening. A solenoid is coupled to the catheter at a distal section of the catheter. The catheter extends at least partially into a hollow core of the solenoid so that a ferroadhesive may be delivered through the catheter, through the hollow core, and past the delivery device to the targeted fistula. The solenoid is configured to selectively provide a magnetic field having strength sufficient to hold a bolus of the ferroadhesive at the targeted fistula until the ferroadhesive has sufficiently set.

Certain embodiments are directed to a method of delivering a ferrofluid to a targeted treatment site. The method includes positioning a distal end of a delivery occlusion device near the targeted treatment site, delivering an amount of a ferrofluid through a catheter of the delivery device and past a distal opening of the delivery device to the targeted treatment site, and actuating a solenoid of the device to generate a magnetic field to hold at least a portion of the ferrofluid at the targeted treatment site. In some embodiments, the targeted treatment site is a pathological fistula, and the ferrofluid is a ferroadhesive. In some embodiments, the method includes maintaining position of the delivered ferroadhesive at the fistula until the ferroadhesive has sufficiently solidified.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

One or more embodiments described herein relate to devices configured for forming an occlusion at a targeted treatment site within a body, such as to plug a pathological fistula. At least some of the embodiments disclosed herein include a catheter having an interior lumen extending to a distal opening at the distal end of the catheter. A distal section of the catheter is configured as a solenoid operable to selectively generate a magnetic field at the vicinity of the distal section of the catheter. In certain implementations, the generated magnetic field provides control over a bolus of magnetically responsive adhesive delivered through the lumen of the catheter and exiting out of the distal opening of the catheter. Beneficially, in some embodiments, the solenoid is configured as a hollow solenoid disposed in mechanical relationship with the catheter so as to allow use of the catheter for the delivery of occlusion-forming adhesive materials and other materials. Alternatively, a solenoid having a solid core is disposed within a catheter so as to provide inter-luminal space between the outer diameter of the solenoid and the inner diameter of the catheter to enable the delivery of a ferroadhesive through the inter-luminal space. One or more embodiments described herein therefore enable positional control of a delivered bolus of tissue adhesive, thereby providing more effective treatment of pathological fistulae.

Embodiments of the present disclosure may be configured for use in a variety of treatment settings. For example, the device and methods may be used in the closure of fistulas (such as enterocutaneous, biliary, rectovaginal, enterovesicle, enterourethral, esophageal, etc.), in the treatment of biliary or pancreatic duct leaks, and in the treatment of gastric varices, ateriovenous malformations, and vascular aneurysms. In particular, aspects of the present disclosure are directed to occlusion devices and methods of forming occlusions that allow precise locational control of a bolus of occlusion-forming material (e.g., glue/adhesive). In at least some embodiments, the occlusion device is configured to be detachable and extractable from a forming or formed occlusion without disrupting the occlusion or surrounding tissues or structures.

Although many of the exemplary embodiments are described herein in the context of delivering an adhesive or glue material for forming an occlusion to treat a fistula, it will be understood that the principles described herein may also be applied in other uses or treatment contexts. For example, described features may be applied generally to other treatment contexts involving the controlled delivery of a ferrofluid (adhesive or non-adhesive) to a treatment site (fistula or non-fistula).

Figure 1A:
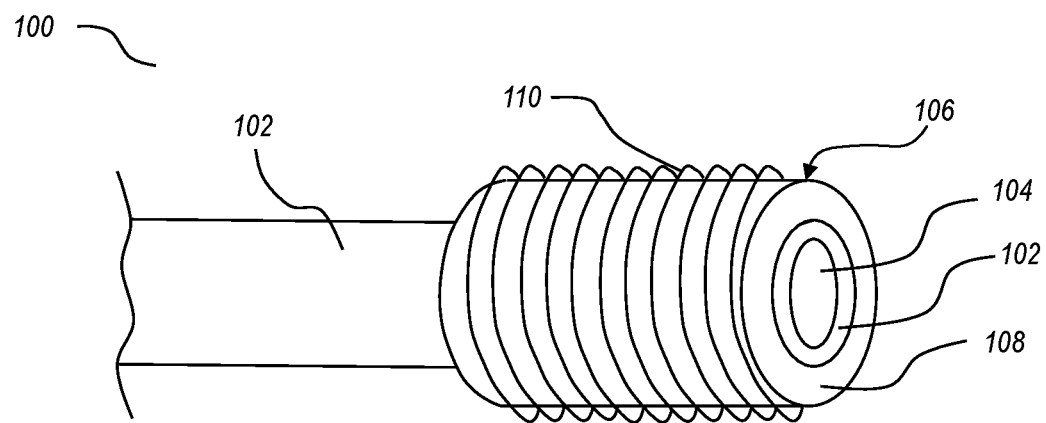
FIG. 1A illustrates an embodiment of a hollow solenoid delivery device configured to deliver a ferrofluid.

FIG. 1A illustrates an embodiment of an occlusion device 100 configured to enable delivery of and positional control over an occlusion-forming tissue adhesive. As shown, the occlusion device 100 includes a catheter 102. The catheter 102 includes an interior lumen extending to a distal opening 104. A distal section of the catheter 100 includes components and features enabling the distal section to function as a solenoid 106. As shown, the solenoid 106 includes a core 108 and a coil 110 surrounding the core 108. In some embodiments, the coil 110 is coupled to one or more leads (not shown) extending proximally from the solenoid 106 to a power supply for supplying power to the solenoid 106 (e.g., any source of sufficient power, such as a battery powered supply and/or a connection to a wall outlet). For example, the one or more leads may extend through one or more lumens provided within the catheter 102.

In the illustrated embodiment, the solenoid 106 is configured with a hollow structure so as to provide an interior lumen through which the catheter 102 may at least partially extend or through which the lumen of the catheter 102 may join. The hollow structure of the solenoid 106 thereby enables fluid (e.g., a ferrofluid and/or other materials) to be delivered through the catheter 102, through the solenoid 106, and through the distal opening 104 to a targeted area distal from the solenoid 106 and distal opening 104.

In the illustrated embodiment, the solenoid 106 is configured to, upon receiving electrical current, generate a magnetic field for influencing the positioning of a magnetically-responsive material, such as a magnetically-responsive tissue adhesive delivered through the catheter 102. The generated magnetic field can function to maintain the location of the adhesive. For example, the generated magnetic field provided by the activated solenoid 106 can prevent the adhesive material from locating to and/or adhering to undesired areas, such as adjacent ducts and vascular structures. The illustrated solenoid 106 may therefore function as an electromagnet capable of being selectively activated and deactivated in response to application of electrical current. In addition, the strength of the generated magnetic field may be manipulated by adjusting the current and/or voltage supplied to the solenoid 106. In at least some implementations, this beneficially enables fine-tuned control over the positional manipulation of a bolus of magnetically responsive adhesive.

In embodiments described herein, the term "catheter" is used to denote a structure having one or more lumens and that is suitable for routing to a targeted anatomical treatment site, such as a pathological fistula. Catheters may have any size suitable for a desired application. For example, catheters may have an inner diameter or an outer diameter within a range of 3 to 34 Fr, or about 5 to 26 Fr. The catheters described herein may be used in conjunction with an endoscope system (e.g., with a distally positioned camera), such as for use as a colonoscope in an enterocutaneous fistula repair procedure. One or more embodiments described herein may also be used in conjunction with imaging modalities to aid in proper positioning of the occlusion device. For example, an occlusion device may be utilized in conjunction with X-ray, fluoroscopy, ultrasound, infrared, other imaging modalities, or combinations thereof.

As used herein, the terms "magnetically responsive fluid," "magnetically responsive adhesive," "magnetically responsive glue," and the like refer to substances that are deliverable to a targeted treatment site and which are capable of being positionally manipulated in response to an imparted magnetic field. The term "ferrofluid" is used herein to refer to a magnetically responsive fluid formed as a suspension of ferrous particles (e.g., nano- or micro-sized) within a carrier. A ferrofluid includes particles sized such that Brownian motion of the particles prevents particle alignment and allows the ferrofluid to function as a paramagnetic material (i.e., a material that only maintains a magnetic moment during exposure to a magnetic field).

In some embodiments, a ferrofluid includes a suspension of particles where the particles have an average particle diameter of about 5 to 15 nm, or about 8 to 12 nm. In some embodiments, the ferrous particles are suspended along with a surfactant, such as an anionic surfactant. In some embodiments, the ferrofluid includes ferroparticles at a concentration of about 0.1 to 3 g/ml, about 0.5 to 2 g/ml, about 0.75 to 1.5 g/ml, or about 1.3 g/ml. One exemplary ferrofluid, which is available under the trade name EMG 700, includes ferroparticles having a nominal particle diameter of about 10 nm, included at a concentration of about 1.29 g/ml suspended in water along with an anionic surfactant. The ferrofluid may be combined with water, saline, other fluids, or combinations thereof according to particular application needs.

As used, herein, the term "ferroadhesive" refers to a particular type of ferrofluid including ferrous nanoparticles suspended within an adhesive carrier material. For example, the adhesive carrier can include a biocompatible cyanoacrylate material, fibrin glue, other adhesive suitable for medical or surgical use, or combinations thereof. By way of another example, a ferrofluid may be blended with a suitable adhesive to form the ferroadhesive. In some embodiments, the ferrofluid is included, by weight of the resulting ferroadhesive, at about 10, 20, 30, 40, 50, 60, 70, 80, or 90%, or at a concentration within a range having endpoints defined by any two of the foregoing values. Although particular examples described herein may refer specifically to ferroadhesive or other particular type of magnetically responsive material, it will be understood that the alternative embodiments may substitute the ferroadhesive for other magnetically responsive materials that are known in the art or which may be discovered.

In the embodiment illustrated in FIG. 1A, the core 108 encompasses the distal section of the catheter 102. The core 108 is preferably formed from one or more materials providing high magnetic permeability. Presently preferred embodiments include iron. Alternative embodiments may include metallic glass, mu-metal, cobalt-iron alloys, nickel-iron alloys (e.g., permalloy), ferritic stainless steel, martensitic stainless steel, magnetically permeable ceramics (e.g., ferrite), or combinations thereof.

In some embodiments, the core 108 is formed as a solid integral piece of material. In other embodiments, the core 108 includes separate sections, such as a laminate structure of multiple layers. For example, as explained in more detail below, some embodiments include a core formed from one or more layers of wire (e.g., formed in a coil around a catheter) coated with a paint to fill in interstitial gaps between adjacent sections/coils of the wire. The wire and/or paint are preferably formed from one or more of the highly permeable materials described herein (e.g., iron). Subsequent examples refer particularly to iron wire and iron paint embodiments. However, it will be understood that in alternative embodiments, the wire and/or paint components may include one or more of the alternative highly magnetically permeable materials described herein.

The solenoid 106 may be provided with a longitudinal length tailored for a particular application or set of applications. In some embodiments, the solenoid has a length of about 0.5 cm, 1 cm, 2 cm, 3, cm, 4 cm, 5 cm, or a length within a range defined by any two of the foregoing values. For example, beneficial results have been shown using a solenoid 106 having a length within a range of about 1 to 3 cm.

In the illustrated embodiment, the inner diameter of the hollow solenoid 106 is defined by the catheter 102 to which the core 108 of the solenoid 106 encompasses. The inner diameter may be configured to suit a particular application or set of applications. In at least some embodiments, the inner diameter measures about 0.5 mm, 0.75 mm, 1 mm, 1.5 mm, 2 mm, 3 mm, 5 mm, 10 mm, 15 mm, or measures within a range defined by any two of the foregoing values. For example, beneficial results have been shown using a device having an inner diameter of about 1 mm.

In the illustrated embodiment, the outer diameter of the hollow solenoid is defined at least in part by the thickness of the core 108 and the thickness of the coil 110. The outer diameter may be configured to suit a particular application or set of applications. In at least some embodiments, the outer diameter measures about 1 mm, 1.5 mm, 2 mm, 3 mm, 5 mm, 10 mm, 15 mm, 18 mm, or measures within a range defined by any two of the foregoing values. For example, beneficial results have been shown using a device having an outer diameter of about 1.5 to 4 mm.

The coil 110 may be formed from one or more electrically conductive materials, such as copper, gold, silver, other conductive materials, or combinations thereof. In some embodiments, the coil 110 is formed from a wire material having a diameter measuring about 0.08 mm, 0.1 mm, 0.14 mm, 0.18 mm, 0.25 mm, 0.4 mm, 0.7 mm, 1 mm, or measuring within a range defined by any two of the foregoing values. For example, beneficial results have been shown using a coil made from wire having a diameter within a range of about 0.33 mm to 0.66 mm. The coil 110 may be wrapped around the core 108 by an amount necessary for a particular application or set of applications. In some embodiments, the coil is wrapped around the core 110 to provide a turns per unit length value (where unit length refers to longitudinal length of the core 108) of about 5 turns/cm, 10 turns/cm, 20 turns/cm, 40 turns/cm, 60 turns/cm, 100 turns/cm or a turns per unit length measurement within a range defined by any two of the foregoing values. For example, beneficial results have been shown using a turns per unit length value of about 15 to 20 turns/cm.

Figure 1B:
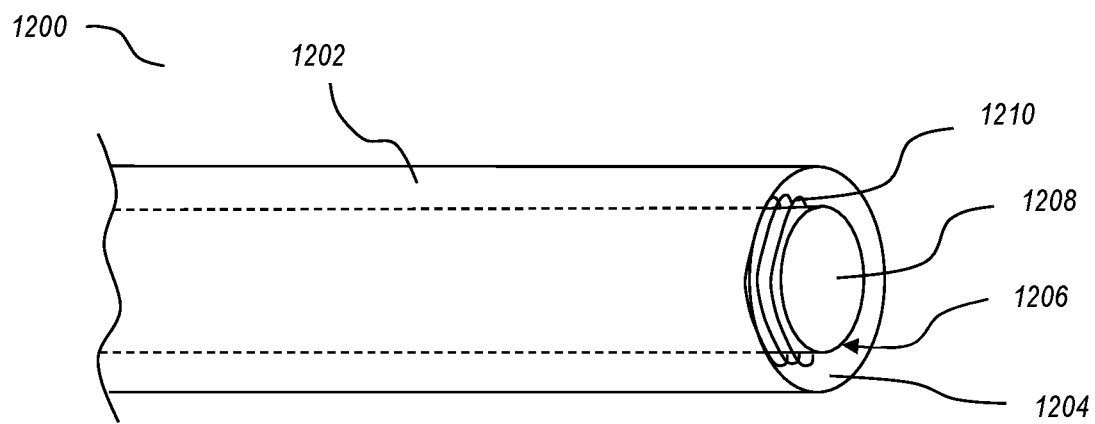
FIG. 1B illustrates another embodiment of a solenoid delivery device having a solid core solenoid disposed within a catheter configured to deliver a ferrofluid.

FIG. 1B illustrates an alternative embodiment of an occlusion device 1200 in which a solenoid 1206 is disposed within a catheter 1202 in a manner so as to define an inter-luminal space between the outer diameter of the solenoid 1206 and the inner wall of the catheter 1202. The illustrated embodiment may otherwise be configured similar to the embodiment of FIG. 1A (with respect to material selection, sizes, operational characteristics, etc.). In this embodiment, the solenoid core 1208 is formed as a solid component, and the coil 1210 wrapped around the core 1208 is also disposed within the inter-luminal space. In operation, rather than passing a ferrofluid through a lumen within the solenoid, as with the embodiment of FIG. 1A, the fluid may be passed through the inter-luminal space between the catheter 1202 and the solenoid 1206 and through the distal opening 1204.

Figure 2A:
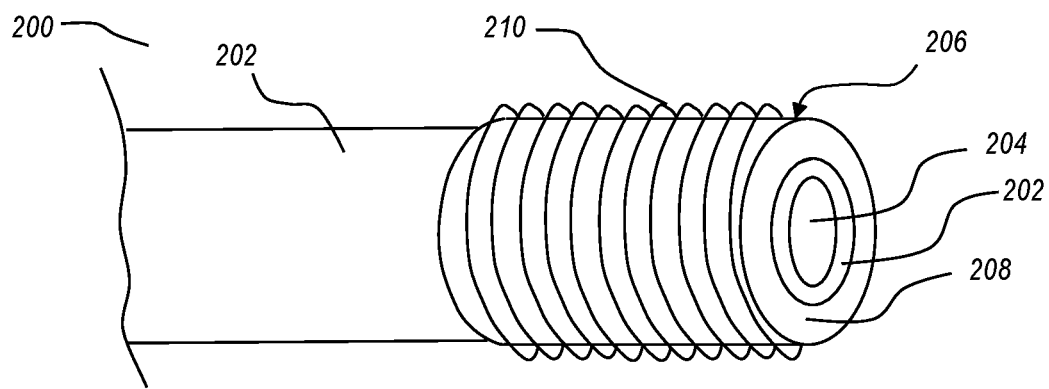
FIGS. 2A and 2B illustrate another embodiment of a hollow solenoid delivery device having a tapered catheter component.
Figure 2B:
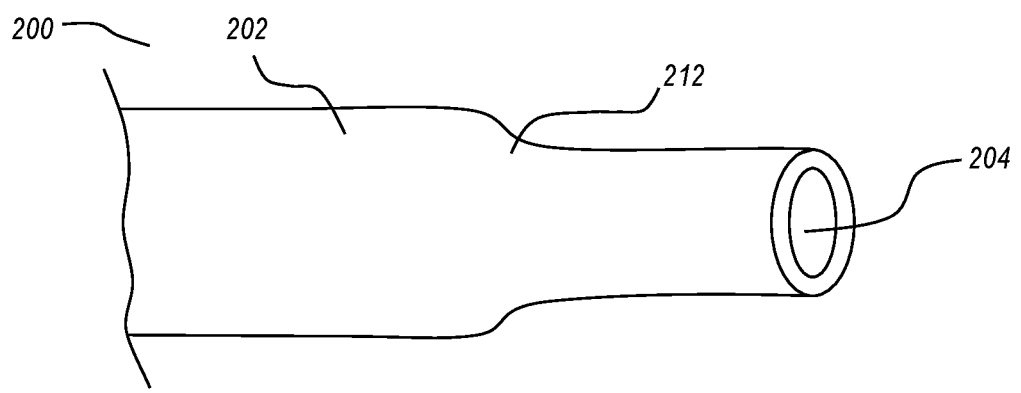

FIGS. 2A and 2B illustrate an alternative embodiment of an occlusion device 200 in which the catheter 202 is shaped so as to maintain a substantially flush outer diameter between the solenoid 206 and the more proximal sections of the catheter 202. FIG. 2A illustrates the occlusion device 200 including a solenoid 206 (having a core 208 and a coil 210) and a catheter 202 extending through the core 208 to a distal opening 24 (similar to the embodiment illustrated in FIG. 1A). As shown, the outer diameter of the solenoid 206 is substantially aligned with the outer diameter of the catheter 202 as the catheter 202 extends proximally from the solenoid 206. FIG. 2B illustrates the occlusion device 200 with the solenoid 206 removed so as to show a tapered section 212 of the catheter 202.

The tapered section 212 may be configured in size and shape to provide a desired relationship between the catheter 202 and the solenoid 206. In the illustrated embodiment, the tapered section 212 is configured to provide a substantially continuous outer diameter between the solenoid 206 and the proximally extending section of the catheter 202. In other embodiments, the catheter 202 may include a differently configured tapered section 212 and/or other structural components to provide a different positional relationship between the solenoid 206 and the catheter 202. For example, the difference in outer diameter between the catheter 202 and solenoid 206 may be set according to the structure of the tapered section 212. In some embodiments, for example, the outer diameter of the solenoid 206 may be smaller than the outer diameter of other more proximal sections of the catheter 202.

FIGS. 3A-3D illustrate cross-sectional views of various embodiments of occlusion devices. In FIGS. 3A-3D, the cross-sections are taken at distal sections of the devices where both catheter and solenoid components are engaged with one another. FIGS. 3A-3D may include one or more components described in relation to FIGS. 1A to 2B, as well as other embodiments described herein, and the corresponding description may therefore be applied to the embodiments of FIGS. 3A-3D as applicable.

Figure 3A:
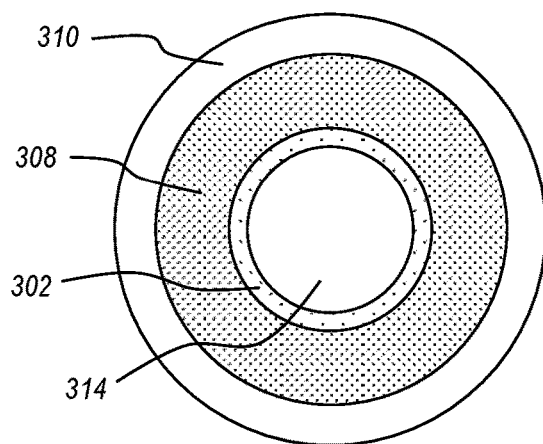
FIGS. 3A to 3D illustrate cross-sectional views of various embodiments of hollow solenoid delivery devices.
Figure 3B:
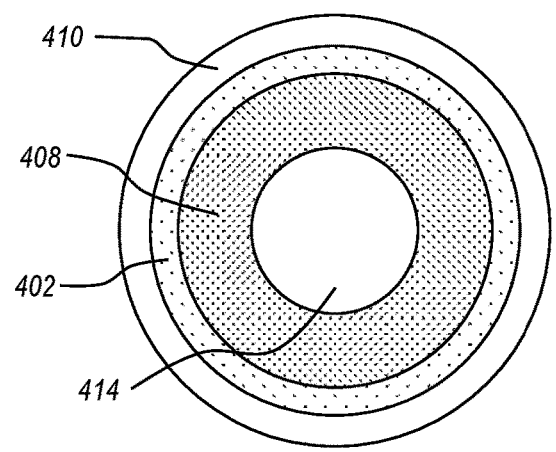
Figure 3C:
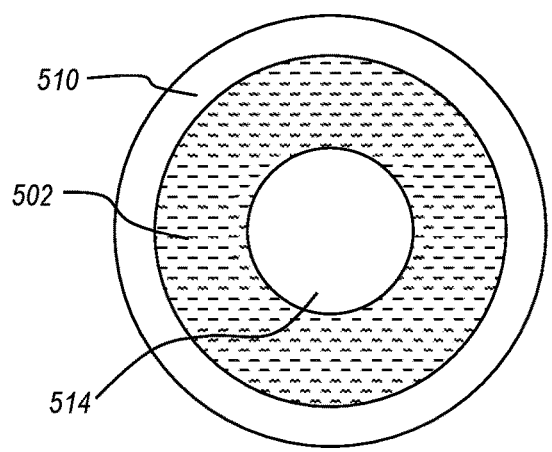
Figure 3D:
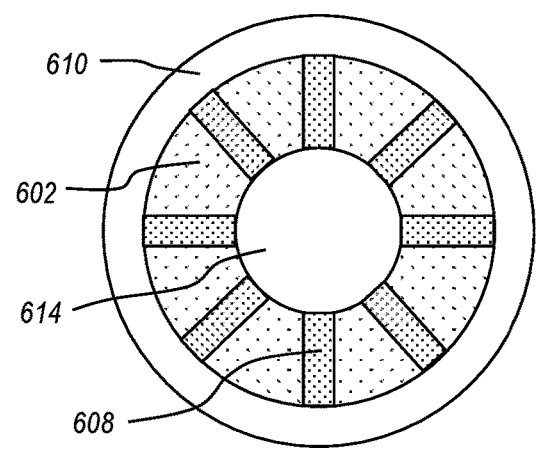

FIG. 3A illustrates an embodiment in which a catheter 302 defines a central lumen 314. The catheter 302 is encompassed by a solenoid core 308. The solenoid core 308 is encompassed by a solenoid coil 310. FIG. 3B illustrates an embodiment in which a solenoid core 408 defines a central lumen 414. The solenoid core 408 is encompassed by a catheter 402. The catheter 402 is encompassed by a solenoid coil 410. FIG. 3C illustrates an embodiment in which a catheter 502 defines a central lumen 514. In this embodiment, at least a portion of the catheter 502 includes an amount of embedded ferrous particles (e.g., iron and/or other materials having high magnetic permeability as described herein) so as to enhance the magnetic permeability of the catheter. The catheter 502 is encompassed by a solenoid coil 510. FIG. 3D illustrates an embodiment in which a catheter 602 defines a central lumen 614. In this embodiment, the catheter 602 includes a number of strips 608 of ferrous material (e.g., iron and/or other materials having high magnetic permeability as described herein) so as to enhance the magnetic permeability of the catheter 602. The catheter 602 is encompassed by a solenoid coil 610.

The embodiments shown in FIGS. 3A-3D are beneficially arranged to provide solenoids having a hollow configuration. Such embodiments are capable of providing selective electromagnetic functionality while also providing a central lumen through which a ferrofluid may be effectively routed. Advantageously, one or more embodiments described herein are capable of effectively delivering a ferrofluid to a targeted area while also directing a generated magnetic field toward the same targeted area. One or more of the described embodiments are thereby able to align the generated magnetic field with the delivery path of the ferrofluid, enabling effective control over the position of the delivered ferrofluid. In contrast, an occlusion device in which a solenoid or other magnetic field generator is offset from or otherwise not aligned with a delivery catheter will generate a magnetic field not in axial alignment with the delivery path of any delivered ferrofluid or other delivered material. Such an offset/misaligned configuration can reduce the ability to effectively manipulate an amount of delivered ferrofluid.

Figure 4:
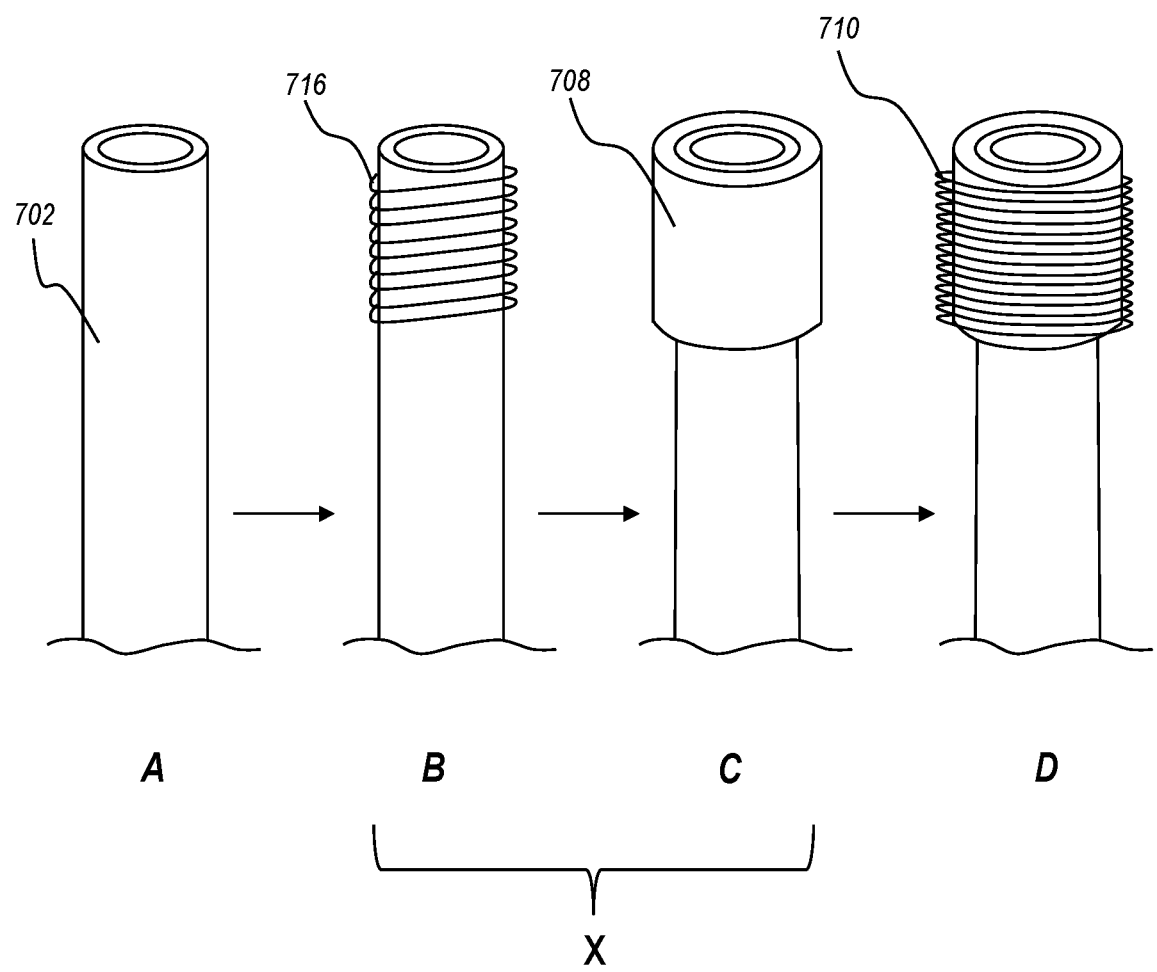
FIG. 4 illustrates an exemplary manufacturing process for manufacturing a hollow solenoid delivery device.

FIG. 4 illustrates an embodiment of a manufacturing process for forming an occlusion device, such as one or more of the occlusion device embodiments described herein. As shown in step "A," a catheter 702 having at least one lumen is provided. The catheter 702 may have a substantially uniform cross-section, as shown, or may have a discontinuous cross-section (e.g., tapered as in FIGS. 2A and 2B or otherwise tapered). The catheter 702 may have a circular cross-section, as shown, or may have a cross-section including one or more portions having cross-sectional shapes that are ovoid, polygonal, erratic, or otherwise shaped. The catheter 702 is configured for effective delivery of a ferrofluid through the at least one lumen. In preferred embodiments, the catheter 702 is configured for effective delivery of a ferroadhesive, such as a cyanoacrylate tissue glue having a concentration of ferrous nanoparticles effective to impart magnetic responsiveness to the tissue glue.

In step "B," a distal section of the catheter 702 is wrapped in a wire 716 formed from a magnetically permeable material. In presently preferred embodiments, the wire 716 comprises iron. In other embodiments, a wire formed from one or more additional or alternative materials having high magnetic permeability may be utilized. The wire 716 may be packed tightly around the distal section of the catheter 702 so as to form a base for the solenoid core of the device. The wire may be configured in size so as to provide a solenoid having desired electromagnetic properties (e.g., desired for a particular application or set of applications). In some embodiments, the wire 716 has a diameter measuring about 0.08 mm, 0.1 mm, 0.14 mm, 0.18 mm, 0.25 mm, 0.4 mm, 0.7 mm, 1 mm, or measuring within a range defined by any two of the foregoing values. For example, beneficial results have been shown using an iron wire material having a diameter of about 0.35 mm.

In step "C," a coating/paint is applied to the wire 716 to fill in interstitial spaces between adjacent turns of the wire 716 so as to form a core 708. The coating is preferably formed from a material having a high magnetic permeability, such as one or more of the materials described with respect to the wire 716. As indicated by the numeral "X," steps B and C may be repeated a number of times to provide a core having desired size, weight, and/or magnetic properties. For example, after a first layer of coating has been applied to form the solenoid core 708, another wire can be wrapped around the core (step B repeated) followed by the application of another layer of coating material (step C repeated).

In some embodiments, the core 708 is configured with 1 to 10 layers, or with 2 to 6 layers. In some embodiments, the core 708 is configured to have a weight within a range of about 0.3 g to 5 g, or about 0.6 g to 3.5 g. For example, iron cores formed within the foregoing weight range have been found to provide beneficial results. In embodiments having cores formed from different materials, the relative weight of the core may be adjusted from the foregoing weight ranges according to proportional differences in density between iron and the different materials. In step "D," a coil 710 is applied (e.g., wrapped around) the outside of the core 710 to complete the solenoid of the occlusion device.

Although the process shown by FIG. 4 illustrates one exemplary method for manufacturing an occlusion device, it will be understood that other processes may also be utilized to produce one or more of the disclosed occlusion devices. For example, although FIG. 4 illustrates the manufacture of a solenoid core 708 using a combination of wire 716 and a coating/paint, other method and/or device embodiments may omit the use of a wire, such as by including pre-formed cores attached (e.g., adhered and/or mechanically fastened) to a catheter.

Figure 5A:
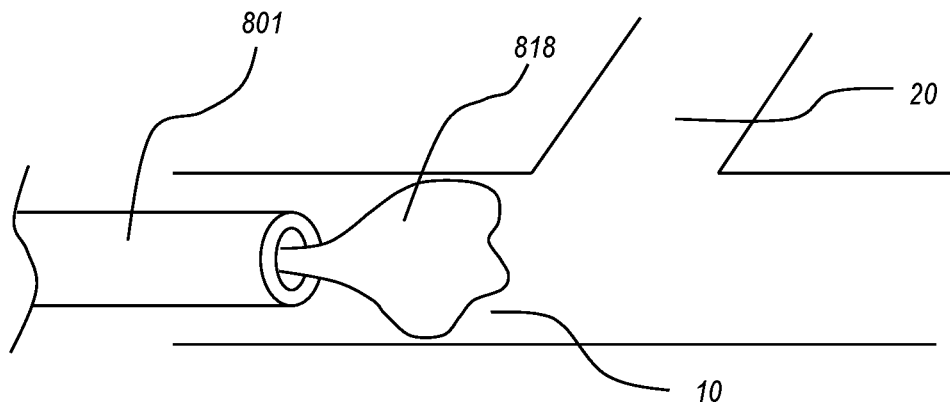
FIGS. 5A and 5B illustrate delivery of a ferrofluid to a targeted treatment site using a delivery catheter not configured to provide a magnetic field for controlling position of the ferrofluid.
Figure 5B:
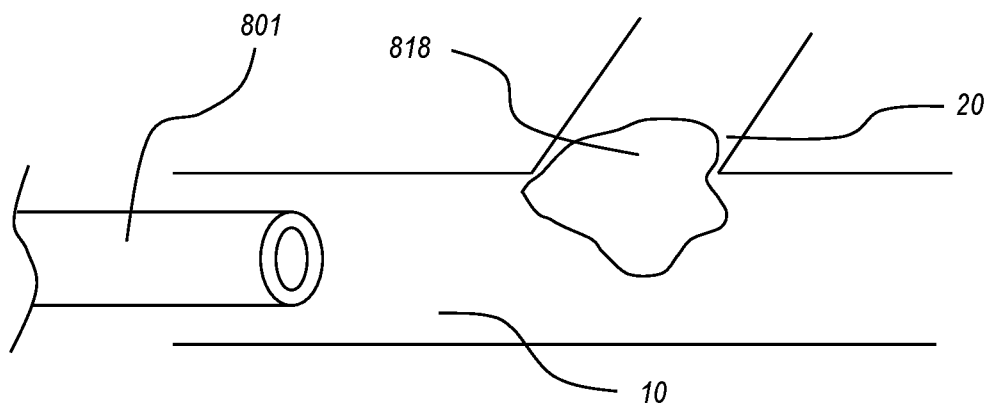

FIGS. 5A and 5B illustrate use of a catheter device 801 to deliver a ferrofluid to a targeted treatment site 10. The illustrated catheter device 801 is not configured with a hollow solenoid and associated electromagnet functionality. As shown in FIG. 5A, a bolus of ferrofluid 818 is delivered through the catheter device 801 near the targeted treatment site 10. However, as shown in FIG. 5B, because the catheter device 801 is unable to control the position of the bolus of ferrofluid 818, the bolus of ferrofluid 818 may undesirably migrate to non-targeted anatomical site 20. For example, the non-targeted anatomical site 20 could be an adjacent duct or vasculature structure which is otherwise healthy. In applications in which the ferrofluid 818 is a ferroadhesive, such a migration can lead to complications related to the formation of unwanted tissue plugs, while also failing to resolve the originally targeted pathology.

Figure 6A:
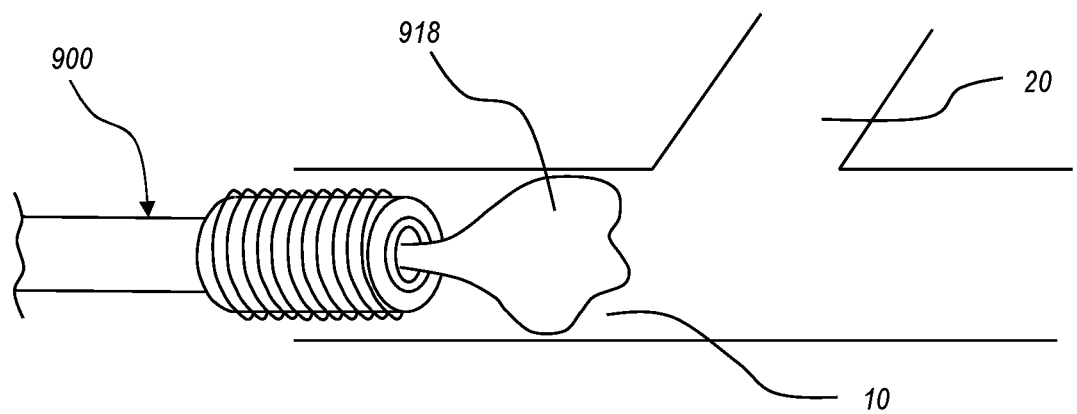
FIGS. 6A and 6B illustrate delivery of a ferrofluid to a targeted treatment site using a delivery device configured to provide a magnetic field for controlling position of the delivered ferrofluid.
Figure 6B:
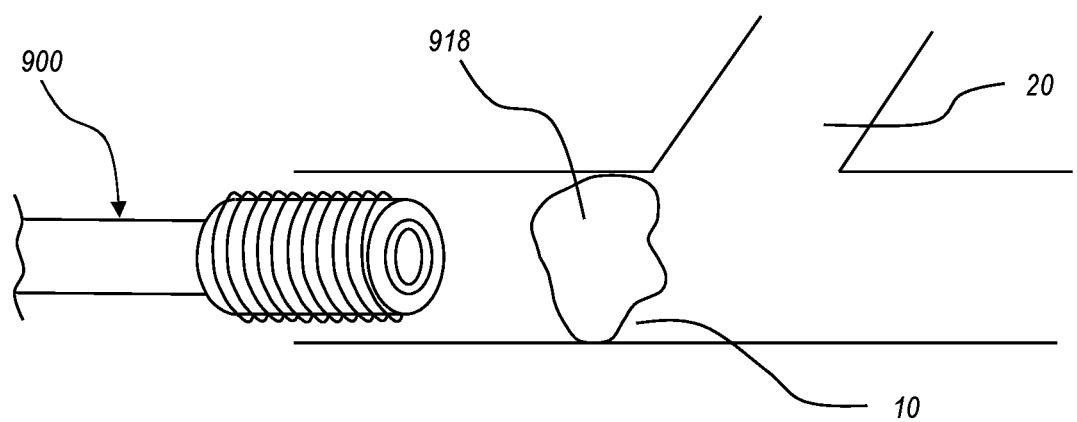

FIGS. 6A and 6B illustrate use of an occlusion device 900 to deliver a ferrofluid to the targeted treatment site 10. The occlusion device 900 may be configured as one of the other occlusion device embodiments described herein, or as a combination of different occlusion device components as described herein. As shown in FIG. 6A, a bolus of ferrofluid 918 is delivered to the targeted treatment site 10. As shown in FIG. 6B, after the ferrofluid 918 has been delivered, the magnetic functionality of the occlusion device 900 is able to maintain the position of the bolus of ferrofluid 918 at the targeted treatment site 10, preventing it from migrating to non-targeted anatomical site 20. For example, in an application in which the ferrofluid 918 is a ferroadhesive, the occlusion device 900 enables the formation of a properly positioned tissue plug at targeted treatment site 10, without damaging or undesirably occluding non-targeted anatomical site 20.

In some embodiments, the occlusion device 900 is configured so as to be able to maintain and/or control the position of a bolus of ferrofluid 918 having a weight of up to about 0.5 g, or up to about 0.75 g, or up to about 1 g, or up to about 2 g. In some embodiments, such activity may be accomplished using an applied current of about 5 amps or less, about 4 amps or less, about 3 amps or less, or about 2.5 amps or less.

In some embodiments, adjustment of one or more components can increase the strength and/or effectiveness of the generated magnetic field, and in some embodiments, the occlusion device 900 may be capable of controlling the position of a bolus of ferrofluid 918 weighing more than 2 g. For example, adjustments to the core (e.g., composition, weight, thickness) and/or adjustments to the coil (e.g., turns per unit axial length, wire composition) can increase the strength of a generated magnetic field. Additionally, or alternatively, increasing applied current can increase the strength of the generated magnetic field. Additionally, or alternatively, adjusting the composition of the associated ferrofluid (e.g., by increasing the concentration of included ferrous particles) can increase the responsiveness of the ferrofluid to the generated magnetic field.

Figure 7A:
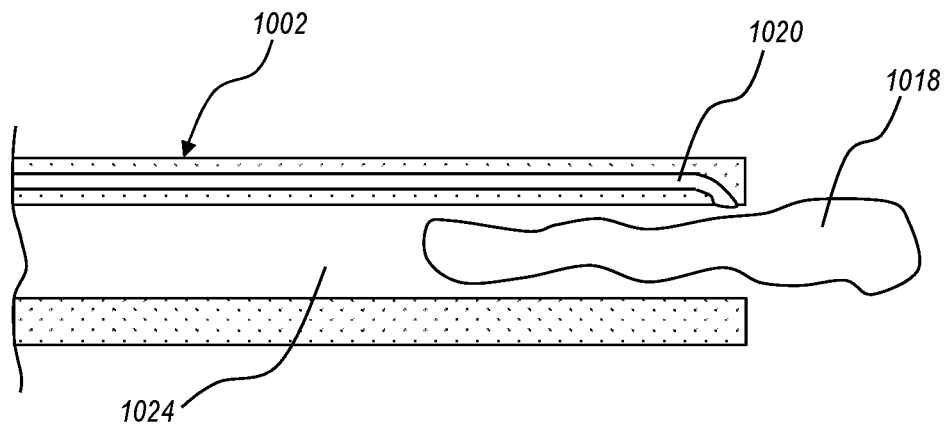
FIGS. 7A and 7B illustrate an embodiment of a catheter having a lumen configured for providing a separating force for separating the catheter from a bolus of delivered ferrofluid.
Figure 7B:
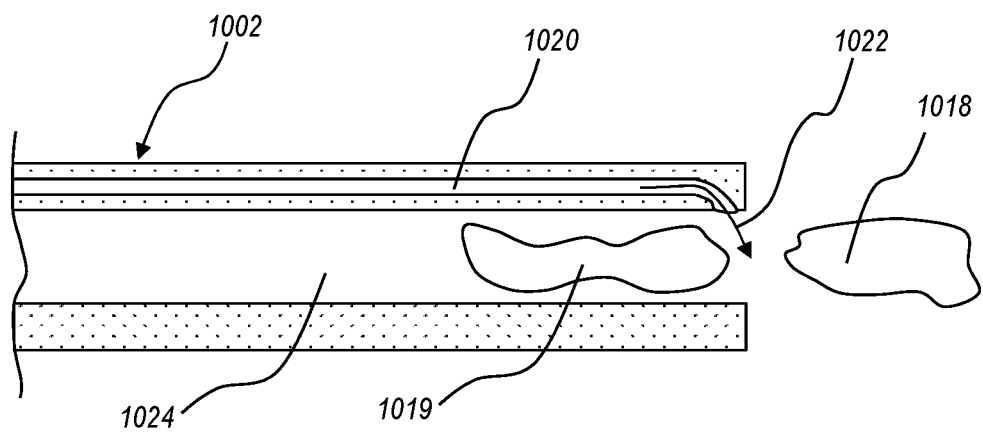

FIGS. 7A and 7B illustrate cross-sectional views of an embodiment of a catheter 1002 that may be utilized with one or more of the occlusion device embodiments described herein. As shown, the catheter 1002 includes a first lumen 1024 configured for delivery of a ferrofluid 1018. As shown in FIG. 7A, in some circumstances, a bolus of delivered ferrofluid 1018 may not completely exit the catheter 1002 when delivered to a targeted treatment site. For example, more ferrofluid may be routed through the catheter 1002 than is necessary to complete the desired treatment and/or an amount external to the catheter 1002 may remain associated with an amount still within the catheter 1002.

Particularly in instances in which the ferrofluid 1028 is a ferroadhesive, complications can result if the bolus of ferrofluid 1018 is not sufficiently separated from the catheter 1002. For example, the catheter 1002 may need to maintain proximity to the ferrofluid 1018 to control the position of the ferrofluid 1018 for a time sufficient to form an effective occlusion, but also needs to avoid getting stuck within the occlusion and needs to be removable from the treatment site without disrupting the newly formed occlusion.

The illustrated catheter 1002 also includes a second lumen 1020 configured to deliver a separating force to separate an external portion of the ferrofluid 1018 from a remaining portion still within the catheter 1002. As shown in FIG. 7B, a fluid (gas and/or liquid) is deliverable through the second lumen 1020, as indicated by arrow 1022, to separate the external portion of the ferrofluid 1018 from an internal remainder 1019. This separation allows the catheter 1002 to be separated from the ferrofluid 1018 while still maintaining proximity to provide control over the position of the ferrofluid 1018.

Figure 8A:
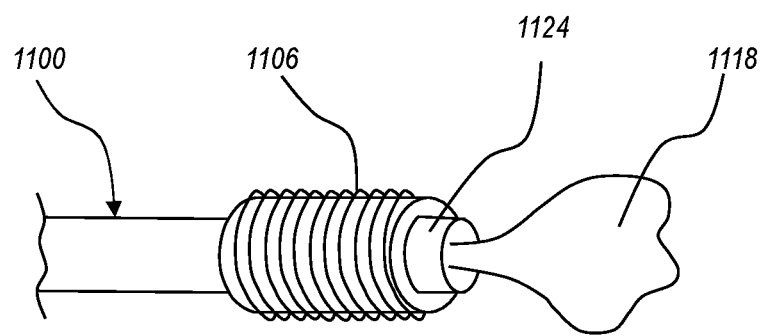
FIGS. 8A and 8B illustrate an embodiment of a delivery device having a breakaway distal section.
Figure 8B:
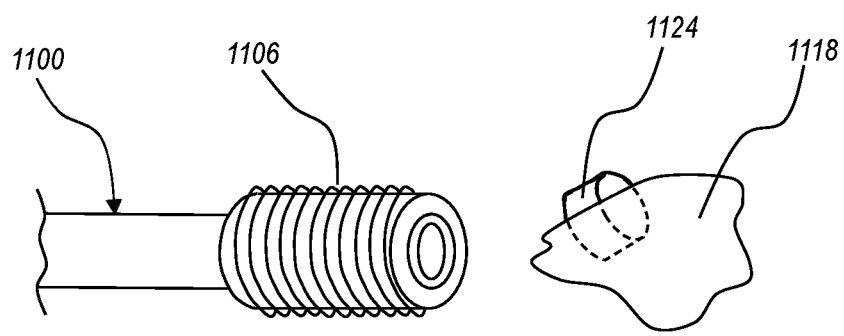

FIGS. 8A and 8B illustrate another embodiment of an occlusion device 1100. The illustrated embodiment is configured with a breakaway distal end 1124. As shown in FIG. 8A, as a ferrofluid 1118 is delivered from the occlusion device 1100, a portion of the ferrofluid 1118 may remain in contact with the device 1100 and/or may not completely separate from the device 1100. As described above, the device 1100 needs to be removable from the ferrofluid 1118 but also is preferably capable of being held in proximity to the ferrofluid 1118 to control the position of the ferrofluid 1118 (e.g., while it cures to form an occlusion). As illustrated in FIG. 8B, the breakaway distal end 1124 is detachable from the solenoid 1106 and other more proximal sections of the device 1100. The breakaway distal end 1124 can remain with the delivered bolus of ferrofluid 1118, allowing the remainder of the device 1100 to be freely repositioned and removed with respect to the ferrofluid 1118.

Examples

Delivery devices were manufactured according to the process illustrated in FIG. 4. The catheters were 5 Fr Bernstein catheters. The cores were formed using alternating layers of iron wire (0.33 mm) and iron paint (49.97% wt. iron). The solenoids had axial lengths of about 2 cm at the distal ends of respective catheters.

Three prototypes of separate experimental groups were built according to the specifications shown in Table 1. Group 2 indicates two alternating coats of iron wire and iron paint were used for the core. Group 3 indicates four alternating coats of iron wire and iron paint were used for the core. Group 4 indicates six alternating coats of iron wire and iron paint were used for the core. A, B, or C indicates the version number of that group. Three versions of each experimental group were built in order to analyze differences between and among prototypes. Weights were taken during the manufacturing process to determine similarity between prototypes of the same number and differences between different group numbers.

TABLE 1

| | Relative Weight (g) Prototype | | | | | | | | |
|---|---|---|---|---|---|---|---|---|---|
| | 2A | 2B | 2C | 3A | 3B | 3C | 4A | 4B | 4C |
| Catheter weight | 0.33 | 0.35 | 0.37 | 0.28 | 0.36 | 0.35 | 0.34 | 0.35 | 0.45 |
| 1 wire | 0.25 | 0.24 | 0.25 | 0.30 | 0.26 | 0.22 | 0.22 | 0.23 | 0.23 |
| 1 paint | 0.02 | 0.02 | 0.02 | 0.02 | 0.03 | 0.04 | 0.04 | 0.02 | 0.03 |
| 2 wire | 0.30 | 0.29 | 0.30 | 0.31 | 0.29 | 0.31 | 0.30 | 0.29 | 0.31 |
| 2 paint | 0.08 | 0.09 | 0.06 | 0.09 | 0.01 | 0.08 | 0.08 | 0.05 | 0.06 |

TABLE 1-continued

| | Relative Weight (g) Prototype | | | | | | | | |
|---|---|---|---|---|---|---|---|---|---|
| | 2A | 2B | 2C | 3A | 3B | 3C | 4A | 4B | 4C |
| 3 wire | | | | 0.30 | 0.38 | 0.35 | 0.39 | 0.35 | 0.37 |
| 3 paint | | | | 0.13 | 0.10 | 0.17 | 0.13 | 0.05 | 0.11 |
| 4 wire | | | | 0.43 | 0.42 | 0.09 | 0.46 | 0.40 | 0.47 |
| 4 paint | | | | 0.18 | 0.17 | 0.54 | 0.27 | 0.18 | 0.21 |
| 5 wire | | | | | | | 0.63 | 0.48 | 0.59 |
| 5 paint | | | | | | | 0.41 | 0.36 | 0.38 |
| 6 wire | | | | | | | 0.76 | 0.77 | 0.90 |
| 6 paint | | | | | | | 0.37 | 0.72 | 0.40 |
| Iron Core Weight | 0.60 | 0.59 | 0.59 | 1.55 | 1.51 | 1.39 | 3.40 | 3.20 | 3.46 |
| Avg | | 0.59 | | | 1.48 | | | 3.35 | |
| Stdev | | 0.00 | | | 0.08 | | | 0.14 | |

Coat number and material in the left column indicate the step in the manufacturing process depicted in FIG. 6 at which the weight was taken. For instance: 3 paint means the weight of the prototype after alternating 3 coats of wire and 3 coats of paint were applied to the core.

After drying, an external coil was constructed using coated copper wire with a diameter of 0.33 mm wrapped tightly approximately 35 times around the iron core. This coil was connected to the power supply in order to create the magnetic field.

Three sets of experiments were conducted to verify the presence of a magnetic field. In the first setup, each prototype was set in a slim track and secured. A 3 mm steel ball was placed 3 mm away from the distal end of the solenoid and the power supply was turned on. The current through the external coil was increased until the magnetic field pulled the steel ball towards the solenoid. The voltage, current, and power were recorded at this instant. The power was turned off and the ball was returned to the start position. Every third trial the entire setup was redone to address potential setup bias. Nine trials were performed for each of the six prototypes in experimental groups 2 and 3. Group 4 was excluded from this experiment because its large size did not fit in the track. It also was much larger than the diameter of the steel ball used.

Each prototype moved the ball within the limits of the power supply, no more than 3A of current. Results indicate that solenoids on this scale can be used to move magnetically reactive materials. Tables 2 to 4 show the results for each of the prototypes evaluated in the horizontal experimental setup.

TABLE 2

| | Current | |
|---|---|---|
| Prototype | Mean (A) | Std. Dev. |
| 2A | 2.62 | 0.25 |
| 2B | 2.05 | 0.13 |
| 2C | 2.37 | 0.25 |
| 3A | 2.29 | 0.41 |
| 3B | 2.58 | 0.25 |
| 3C | 2.73 | 0.16 |

TABLE 3

| | Voltage | |
|---|---|---|
| Prototype | Mean (A) | Std. Dev. |
| 2A | 1.46 | 0.15 |
| 2B | 1.08 | 0.09 |
| 2C | 1.28 | 0.13 |
| 3A | 1.30 | 0.29 |
| 3B | 1.69 | 0.14 |
| 3C | 1.75 | 0.07 |

TABLE 4

| | Power | |
|---|---|---|
| Prototype | Mean (W) | Std. Dev. |
| 2A | 3.89 | 0.76 |
| 2B | 2.21 | 0.31 |
| 2C | 3.04 | 0.63 |
| 3A | 3.07 | 1.26 |
| 3B | 4.39 | 0.75 |
| 3C | 4.79 | 0.48 |

In a second experimental setup, prototype was secured vertically and connected to the power supply. The power was turned to a maximum level of approximately 3A, and the 3 mm steel ball was allowed to hang off the distal end of the prototype. The power was turned down incrementally until the ball fell off. This experiment was used to determine feasibility of using a clinically applicable total weight. A third setup used two 3 mm steel balls weighing a combined total of 0.7427 g. It was determined through discussion with physicians who would potentially use this device that it needed to be able to lift 0.52 g. The experimental set up accounted for a 50% increase in glue weight. The same procedure was followed as in the second set of vertical experiments. 20 trials were attempted for each prototype.

Prototypes 2A, 2B, 2C and 3B all failed to hold the 2 balls vertically and were thus excluded from the results. Tables 5 to 7 show the results.

TABLE 5

| | Current | |
|---|---|---|
| Prototype | Mean (A) | Std. Dev. |
| 3A | 1.66 | 0.43 |
| 3B | n/a | n/a |
| 3C | 0.76 | 0.48 |
| 4A | 0.73 | 0.42 |
| 4B | 1.18 | 0.67 |
| 4C | 1.66 | 0.49 |

TABLE 6

| | Voltage | |
|---|---|---|
| Prototype | Mean (V) | Std. Dev. |
| 2A | 0.31 | 0.21 |
| 2B | n/a | n/a |
| 2C | 0.64 | 0.18 |
| 3A | 0.54 | 0.33 |
| 3B | 0.76 | 0.48 |
| 3C | 1.17 | 0.36 |

TABLE 7

| | Power | |
|---|---|---|
| Prototype | Mean (W) | Std. Dev. |
| 2A | 1.13 | 0.52 |
| 2B | n/a | n/a |
| 2C | 0.33 | 0.38 |
| 3A | 0.53 | 0.51 |
| 3B | 1.20 | 1.22 |
| 3C | 2.12 | 1.20 |

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any element described in relation to an embodiment of FIGS. 1A-6B may be combinable with any element described in relation to an embodiment of FIGS. 7A to 8B.

The present invention may be embodied in other forms, without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A delivery device configured for delivering a ferrofluid, the device comprising:
    a catheter having a lumen extending to a distal opening at a distal end of the catheter wherein the distal end of the catheter includes a tapered section; and
    a solenoid having a core coupled to the catheter at a distal section of the catheter, the solenoid having an electrically conductive coil disposed around at least a portion of an outer circumferential surface of the core, the solenoid having a distal end, wherein an outer diameter of the catheter proximal the tapered section is substantially aligned with an outer diameter of the solenoid;
    wherein the solenoid and the catheter are operatively disposed relative to one another so as to enable passage of a ferrofluid through the delivery device to the distal end of the solenoid, and
    wherein the solenoid is configured to selectively provide a magnetic field having strength sufficient to hold a bolus of the ferrofluid at a desired treatment site.

2. The device of claim 1, wherein the core is a hollow core configured to enable passage of the ferrofluid through the hollow core to the distal end of the solenoid.

3. The device of claim 2, wherein at least a portion of the tapered section is encompassed by the hollow core.

4. The device of claim 3, wherein the tapered section extends to the distal end of the hollow core.

5. The device of claim 1, wherein the core includes iron.

6. The device of claim 1, wherein the core includes one or more layers of wire and a coating filling in interstitial spaces between the one or more layers of wire.

7. The device of claim 1, wherein the solenoid has a length within a range of 1 to 3 cm.

8. The device of claim 1, wherein, at least at a distal section of the device, the device has an inner diameter within a range of 0.5 to 2 mm.

9. The device of claim 1, wherein the solenoid has an outer diameter within a range of 1.5 to 4 mm.

10. The device of claim 1, wherein the coil has a turns per unit axial length value within a range of 10 to 40 turns per cm.

11. The device of claim 1, wherein the catheter further comprises a second lumen configured to impart a separating force at the distal opening for separating a portion of the bolus of ferrofluid located distally external to the catheter from a portion of the bolus of ferrofluid located within the catheter.

12. The device of claim 11, wherein the second lumen has a second lumen opening at the distal opening.

13. The device of claim 1, wherein the catheter includes a breakaway distal section.

14. A delivery device configured for delivering a ferroadhesive to a targeted pathological fistula in order to occlude the fistula, the device comprising:
    a catheter having a lumen extending to a distal opening at a distal end of the catheter; and
    a solenoid coupled to the catheter at a distal section of the catheter, the solenoid having a hollow core through which at least a portion of the catheter extends, wherein the portion of the catheter is encompassed by the hollow core, the solenoid including an electrically conductive coil disposed around at least a portion of an outer circumferential surface of the core, the solenoid having a distal end;
    wherein the hollow core of the solenoid is configured to enable passage of a ferrofluid through the hollow core and past the distal end of the solenoid to a targeted fistula distally disposed from the device, and
    wherein the solenoid is configured to selectively provide a magnetic field having strength sufficient to hold a bolus of the ferroadhesive at the targeted fistula until the ferroadhesive has sufficiently set.

15. The device of claim 14, wherein the portion of the catheter extending within the hollow core has an inner diameter within a range of 0.5 to 2 mm, and wherein the solenoid has an outer diameter within a range of about 1.5 to 4 mm.

16. A method of delivering a ferrofluid to a targeted treatment site, the method comprising:
    positioning a distal end of a delivery device near the targeted treatment site, the delivery device including:
        a catheter having a lumen and a distal opening; and
        a solenoid coupled to the catheter at a distal section of the catheter, the solenoid having a hollow core and an electrically conductive coil disposed around at least a portion of an outer circumferential surface of the core, the solenoid being configured to selectively provide a magnetic field;
    delivering an amount of a ferrofluid through the catheter and past the distal opening to the targeted treatment site;
    actuating the solenoid to generate a magnetic field, the magnetic field holding at least a portion of the ferrofluid at the targeted treatment site; and
    separating a distal end of the device from the amount of delivered ferrofluid using a separation force delivered through a distal end of the catheter.

17. The method of claim 16, wherein the targeted treatment site is a pathological fistula, and wherein the ferrofluid is a ferroadhesive.

18. The method of claim 17, further comprising maintaining position of the delivered ferroadhesive at the fistula until the ferroadhesive has sufficiently solidified.

19. The device of claim 17, wherein the fluid is a gas.

20. The device of claim 16, wherein the separating force is a fluid deliverable through a second lumen to the distal end of the catheter.

\* \* \* \* \*